US005632738A

United States Patent [19]

Sumi et al.

[11] Patent Number: 5,632,738

[45] Date of Patent: May 27, 1997

[54] PLASTIC BLOW CONTAINER FOR MEDICAL FLUIDS

[75] Inventors: Takehiko Sumi, Yamato; Kazuya Matsumoto, Ayase, both of Japan

[73] Assignees: Kewpie Kabushiki Kaisha, Tokyo-to; Kyoraku Co., Ltd., Kyoto, both of Japan

[21] Appl. No.: 345,361

[22] Filed: Nov. 18, 1994

Related U.S. Application Data

[63] Continuation of Ser. No. 39,335, filed as PCT/JP91/01209, Sep. 12, 1991 published as WO93/04547, Mar. 18, 1993 abandoned.

[51] Int. Cl.$^{6}$ .................................................. A61B 19/00

[52] U.S. Cl. .................. 604/408; 604/403; 128/DIG. 24

[58] Field of Search .......................... 604/403, 407–408, 604/414, 416; 128/DIG. 12, DIG. 24

[56] References Cited

U.S. PATENT DOCUMENTS

| | | | |
|---|---|---|---|
| 2,969,792 | 1/1961 | Milton | 128/DIG. 24 |
| 3,054,401 | 9/1962 | Gewecke | 128/DIG. 24 |
| 3,081,002 | 3/1963 | Tauschinski et al. | 128/DIG. 24 |
| 3,251,390 | 5/1966 | Evans | 128/DIG. 24 |
| 5,023,119 | 6/1991 | Yamakoshi | 604/408 |

FOREIGN PATENT DOCUMENTS

| | | |
|---|---|---|
| 1-140954 | 9/1989 | Japan . |
| 2-37783 | 8/1990 | Japan . |
| 3-118068 | 5/1991 | Japan . |
| 517495 | 2/1971 | Switzerland . |

*Primary Examiner*—John G. Weiss

*Assistant Examiner*—P. Zuttarelli

*Attorney, Agent, or Firm*—Oblon, Spivak, McClelland, Maier & Neustadt, P.C.

[57] ABSTRACT

The present invention relates to a so-called "natural dripping" type plastic container by which medicinal fluids are administered by deformation of the flat shaped body. During natural dripping the accumulation capability for the contained fluids is large and the deformation based on back pressure avoids the occurrence of dead space. In the plastic blow container for medicinal fluids of this invention, in the cross-sectional shape of a flat shaped body the long axis width is more than 2.0 times the short axis width, at the upper end of the body a suspending mechanism is formed, and at the outer of the lower end of the body an opening means is formed, the bottom cross-section of the body on the short axis side the shape of parallel faces is formed as a wedge, while the parallel faces on the long axis side are formed with a tapered funnel shape toward the opening means.

2 Claims, 4 Drawing Sheets

PLASTIC BLOW CONTAINER FOR MEDICAL FLUIDS

This application is a Continuation of application Ser. No. 08/039,335, filed on May 4, 1993, now abandoned, filed as PCT/JP91/01209 on Sep. 12, 1991, published as WO93/04657, Mar. 18, 1993.

TECHNICAL FIELD

The present invention relates to a flexible plastic container that is usable for intravenously administering such medicinal fluids as sugar solutions, electrolytic solutions, blood sugar amplifiers, osmotic diuretics, amino acid solutions, fat emulsion preparations, and high calorie solutions, as well as enteral nutrients, such as high protein nutrients, elemental nutrients and liquid foods. When applied to a so-called "natural dripping" type container, an internally filled medicinal fluid is administered through deformation of the container body by backpressure, thus avoiding the occurrence of dead space. A large fluid accumulating capability during natural drip is also featured in an embodiment as a plastic blow container for medicinal fluids.

BACKGROUND ART

Due to such advantages as not breaking even if dropped and light weight, plastic type medicinal fluid containers have rapidly progressed in recent years. Among these, natural dripping types are widely used, which utilize the flexibility of plastic materials whereby the body portion is deformed for administering the medicinal fluid. When used for natural dripping, since air is not supplied into the container during application, concern as to contaminating organisms entering the container is absent, and there is a hygienic advantage. As an example of a plastic container for medicinal fluids, a container of this type is disclosed in Japanese Laid-Open Patent Publication No. 158955/1989 (referred to below as prior art publication). The art publication indicates a unitized plastic container for medicinal fluids, in which an opening at the upper end of the container body is sealed by a stopper device, and at the bottom end of the body, a suspending fixture is provided.

PROBLEMS RESOLVED BY THE INVENTION

The plastic container for medicinal fluids indicated in the above mentioned prior art publication possesses a "square shoulder" type shape at the the upper end of the body through which the medicinal fluid passes. During natural dripping, backpressure soon ceases, and in the final stage of dripping, a medicinal fluid remainder is left in this portion. The upper portion of the medicinal fluid is mainly used for natural dripping by backpressure and deformation proceeds from the top. For this reason, deformation in the final stage of dripping is at the opening side, thus forming the square shouldered shape. Backpressure transmission is difficult and this portion does not deform, thus producing a dead space during dripping. In addition, since the shape of the square shouldered portion impairs the medicinal fluid accumulating capability, a certain amount of medicinal fluid remains.

The present invention can resolve the above mentioned problems possessed by the conventional blow container when embodied as a plastic blow container for medicinal fluids.

DISCLOSURE OF INVENTION

The present invention relates to a blow process formed plastic blow container for medicinal fluids which possesses a cross-sectional shape in which the long axis width is more than 2.0 times the short axis width, a flat shaped body at the upper end of which a suspending means is formed, and at the center of the bottom end of which an opening means is formed, and at the lower cross-section of the body section, the parallel sides of the short axis form a wedge shape, and the parallel sides of the long axis converge toward a funnel shape.

This invention also features tapered shapes formed at the upper and lower ends of the body section. Particularly at the lower end cross-section short axis, the two parallel sides form a wedge shape with an angle $\alpha$ of less than 60°, and at the long axis side the parallel sides form a tapered funnel shape that converges at an angle $\beta$ of less than 130° toward the opening means.

By these provisions, the blow formed plastic blow container for medicinal fluids comprises a plastic container which in the cross-section shape the long axis width is more than 2.0 times the short axis width, and a flat shaped body at the top end of which a suspending means is formed and at the center of the bottom end of which an opening means is formed.

As a result, a plastic blow container for medicinal fluids is obtained whereby backpressure during natural dripping is applied efficiently to the flat shaped body, an efficient natural dripping mode is obtained; and the bottom end shape of the body is such that in the cross-section short axis width the parallel sides form a wedge shape, and in the long axis the parallel sides converge in a funnel shape toward the opening means to provide a large medicinal fluid accumulating capability and avoid occurrence of dead space.

BRIEF DESCRIPTION OF DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein.

BEST MODE FOR CARRYING OUT THE INVENTION

Following is a description with reference to the figures of a preferred embodiment of this invention as a plastic blow container for medicinal fluids.

A plastic blow container for medicinal fluids 1 is blow formed from comparatively flexible plastic. In this grade plastic, tensile elasticity is 100–4000 kg/cm$^2$ (JISK7113). Among the types of materials suitable for forming this type of plastic are ethylene-vinyl acetate copolymer, high pressure method low density polyethylene, linear low pressure method low density polyethylene, low pressure method medium density polyethylene, $\alpha$-olefin-propylene random copolymer containing 2–20 mol % $\alpha$-olefin or $\alpha$-olefin-propylene block copolymer, flexible polyvinyl chloride, ethyl group elastomer, styrene group elastomer, olefin group elastomer and urethane group elastomer. Also included are multilayer materials with intervening oxygen barrier type plastics such as saponified ethylene vinyl acetate copolymers, polyamids and polyvinyl alcohols formed in layers with these main structures.

Figure 1:
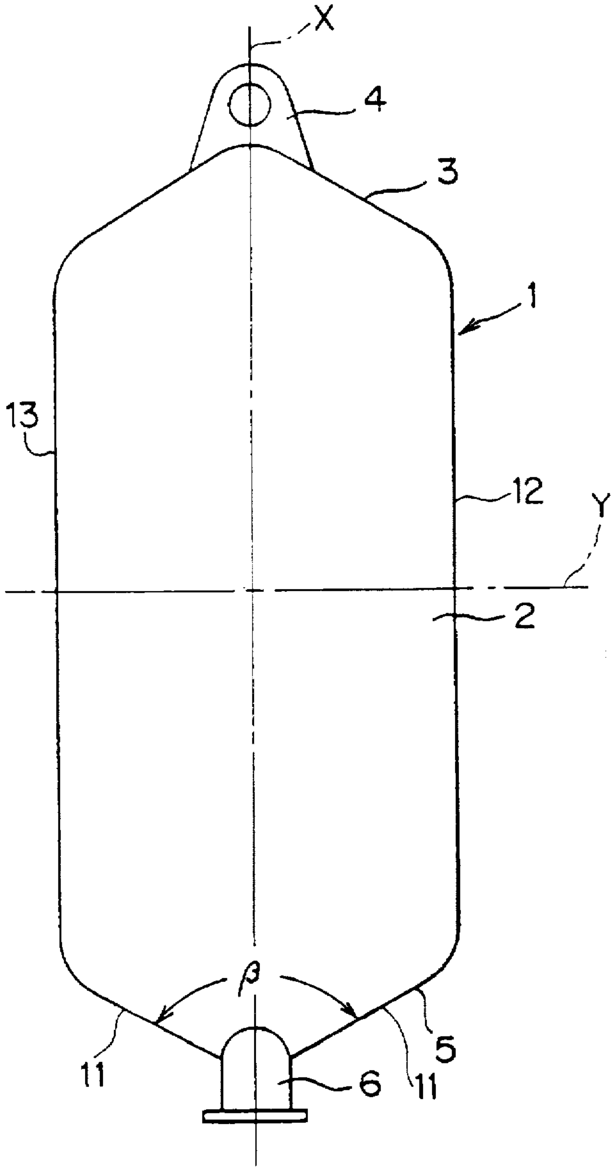
FIG. 1 is a direct view of a plastic flow container for medicinal fluids showing an embodiment of this invention.
Figure 3:
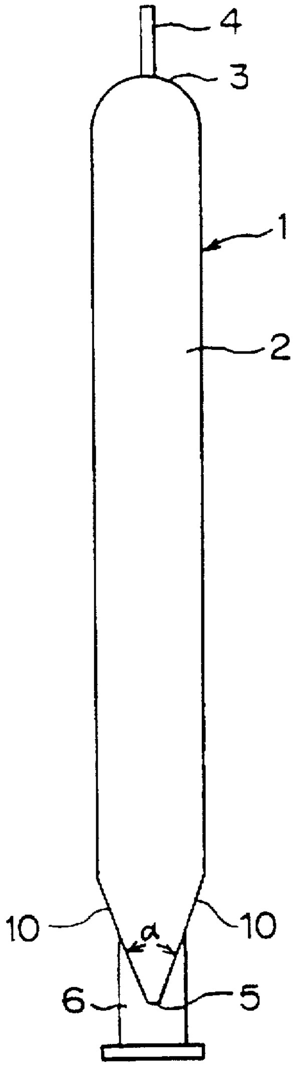
FIG. 3 is a side view of this embodiment.
Figure 2:
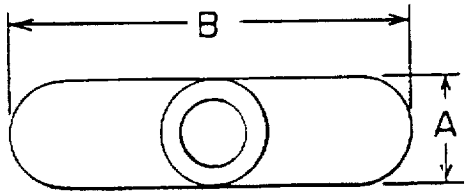
FIG. 2 is a top view of this embodiment.

As shown in FIGS. 1–3, the above type materials can be used to form a plastic blow container for medicinal fluids 1, comprising a flat shaped body 2, at the upper end 3 of which is a suspension means 4 provided as an integral structure of the body 2, and with lower end 5 formed to an opening means 6. The opening means 6 is provided with a stopper means 7 (shown in FIG. 5) which is heat sealed. A central longitudinal axis X and a central transverse axis Y perpendicular to axis X is shown in FIG. 1. Since the cross-section shape of the body 2 is flat, as shown in FIG. 2, with respect to the shorter width-wise dimension A, the ratio of the longer width-wise dimension B to dimension A is about 2.5. First end portions 10,10 are connected to parallel faces of the flat shaped body on sides along the shorter width-wise axis A and converge toward the opening 6. In addition, second end portions 11,11 are connected to parallel faces of the flat shaped body 2 on sides along the longer width-wise axis B and converge toward the opening 6, as shown in FIGS. 1 and 3. If this ratio B/A (flatness) is less than 2.0, deformation by backpressure during natural dripping is reduced and ceases midway. Dripping does not proceed and residual fluid is produced. As shown in FIG. 1, the lower end 5 is convex shaped. In addition, as shown in FIG. 2, the larger width-wise dimension and shorter width-wise dimension terminate at a point where the faces 10, 11 meet faces 12, 13, respectively.

Figure 4:
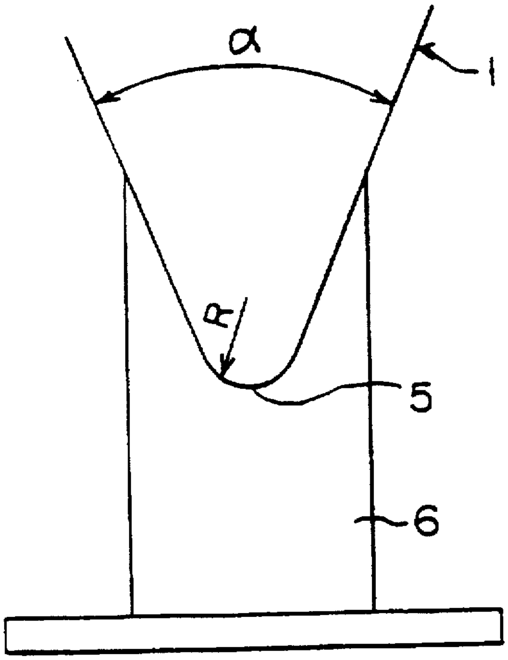
FIG. 4 is an enlarged view of the opening section.

As shown in the FIG. 4 enlargement, at the body 2 bottom cross-section, on the short axis the pair of parallel sides 10, 11 parallel to axis X form a wedge shape at angle α, and on the long axis the pair of parallel sides 12, 13 parallel to axis Y converge in a funnel shape with an angle β toward opening means 6. The pair of faces 10, 11 and the pair of faces 12, 13 are respectively substantially parallel to one another along substantially their entire length, as shown in FIGS. 1 and 3.

Figure 5:
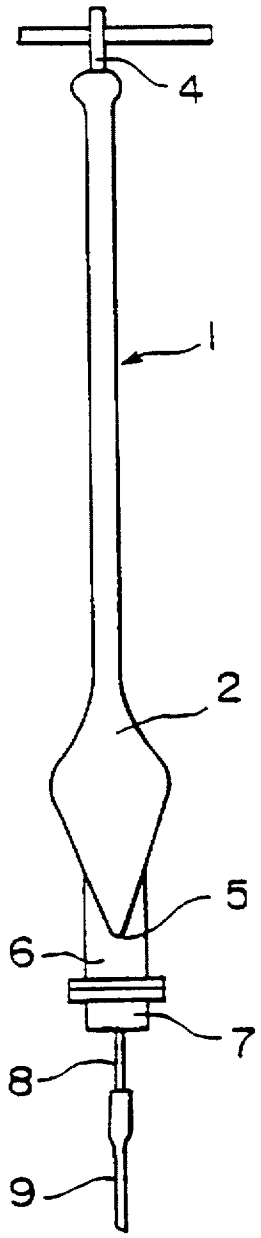
FIG. 5 is a detailed side view of this embodiment when used in the natural dripping mode.

FIG. 5 shows the container state when medicinal fluid is contained and natural dripping is performed. As natural dripping proceeds, deformation is conveyed from the top to the bottom of the body 2. At this time, since the parallel sides of the long axis of the body 2 form a tapering funnel shape which converges toward the opening means 6, during natural dripping the medicinal fluid is efficiently accumulated in the lower portion of the body 2 and discharged.

The above described plastic blow container for medicinal fluids 1 is blow formed of ethylene propylene random copolymer containing 6 mol % ethylene (tensile elasticity 3000 kg/cm$^2$). With respect to the FIG. 1 outline, each section shape is specified in Table 1 for comprising each type of plastic blow container for medicinal fluids. The weight of all of these plastic blow containers for medicinal fluids is 18 g and the average body section thickness is 0.3 mm. At this time, the bottom end radius of curvature R is formed for about 0.15 times the above mentioned angle α.

TABLE 1

| | α (degree) | β (degree) | Flatness | Residual fluid (ml) |
|---|---|---|---|---|
| Embodiment 1 | 45 | 100 | 4.0 | 0 |
| Embodiment 2 | 60 | 100 | 4.0 | 0 |
| Embodiment 3 | 45 | 110 | 4.0 | 0 |
| Embodiment 4 | 45 | 130 | 4.0 | 0 |
| Embodiment 5 | 45 | 100 | 2.0 | 0 |
| Embodiment 6 | 45 | 100 | 3.0 | 0 |
| Embodiment 7 | 45 | 100 | 6.0 | 0 |
| Comparison example 1 | 65 | 100 | 4.0 | 30 |
| Comparison example 2 | 45 | 140 | 4.0 | 0 |
| Comparison example 3 | 45 | 100 | 1.5 | 40 |

These plastic blow containers for medicinal fluids 1 were suspended with the opening means 6 positioned downwards and dripping tests were performed. The containers were filled with 500 ml intravenous fluid (0.9% isotonic saline solution) and 100 ml air. The opening means 6 were provided with internal rubber stoppers by stopper means 7 and heat sealed. Connecting needles 8 were inserted into the stopper means 7. Intravenous needles 9 from the medicinal fluid sets were fixed at the connecting needle 8 position. Medicinal fluid dripped through the intravenous needles 9 was received in messcylinders.

In the dripping test, the time needed for dripping 25 ml, corresponding to 5% of the contained 500 ml medicinal fluid, was first measured and recorded as the initial dripping time ($T_0$). Then the time required for dripping 25 ml ($T_n$) was measured for deriving the dripping speed ratio ($T_n/T_0 \times 100$). This dripping speed ratio was measured until medicinal fluid discharge stopped. Results of these dripping tests of plastic blow containers for medicinal fluids results are shown in FIGS. 6–8.

Figure 6:
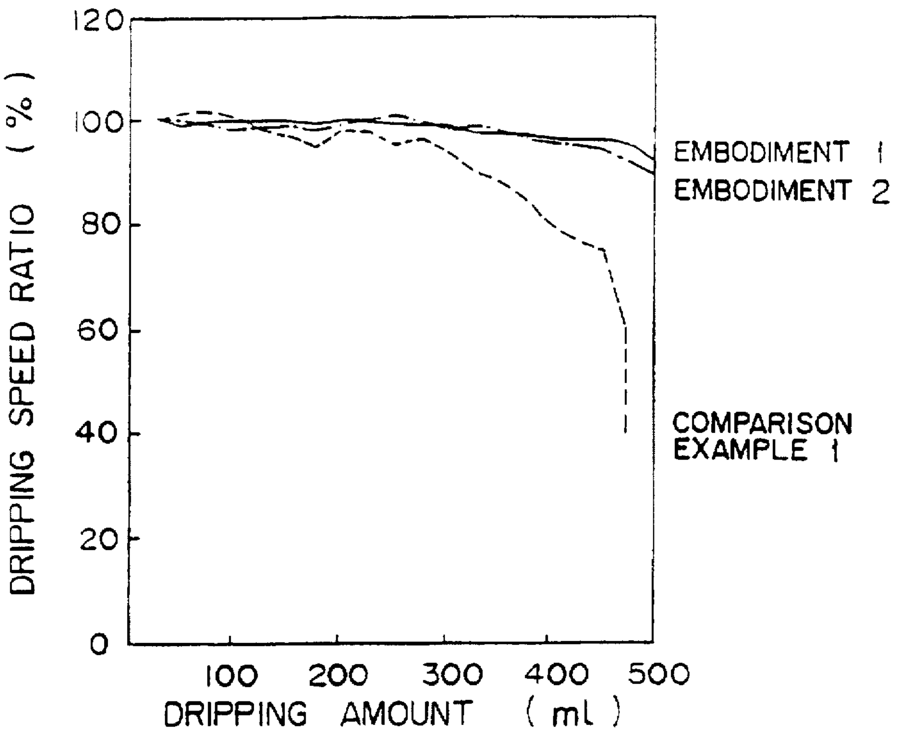
FIGS. 6–8 are graphs indicating relationships between fluid dripping rate and dripping amount.

From FIG. 6, it can be recognized that when α exceeds 60°, variations are produced in the dripping fluid amount (for example in the dripping fluid amount 100–300 ml portion). Moreover, the medicinal fluid dripping cannot proceed to the final amount.

Figure 7:
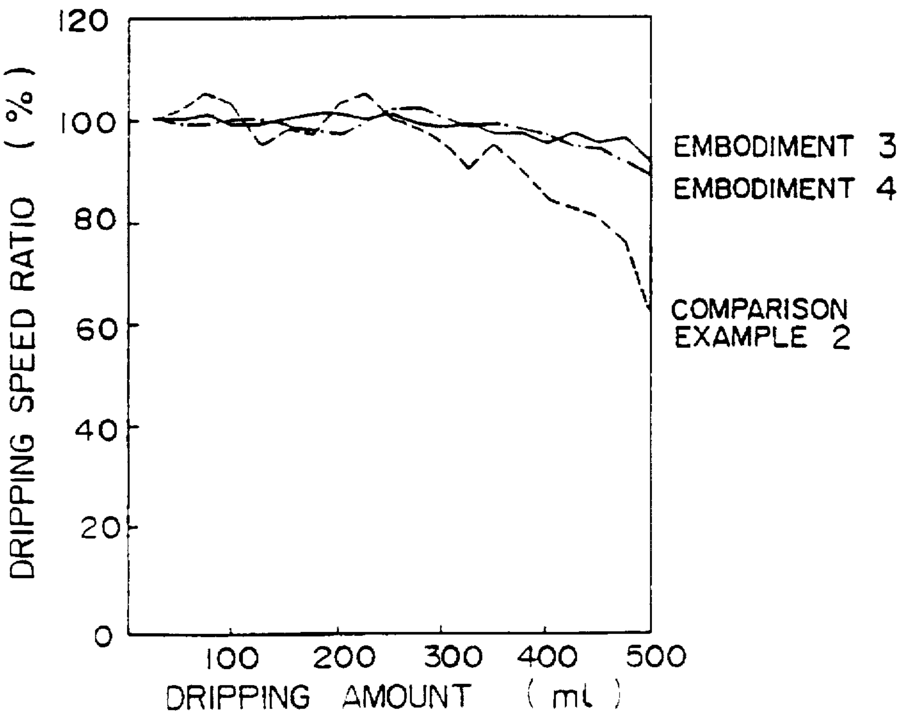

FIG. 7 shows that when β exceeds 130 degrees, even larger variations are produced in the dripping fluid amount and stable discharge cannot be obtained.

Figure 8:
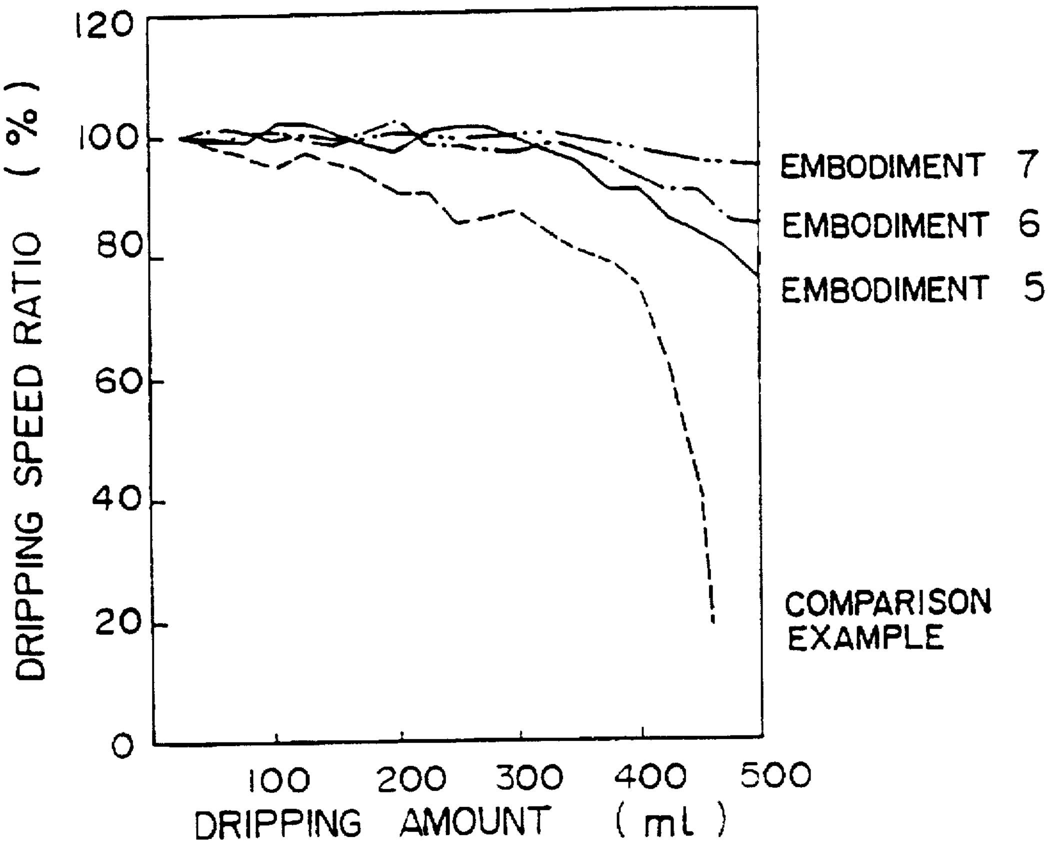

FIG. 8 shows that when flatness is less than 2.0, dripping is not performed to completion. Deformation due to backpressure ceases midway in dripping and a large amount of medicinal fluid remains.

Consequently, by adopting the embodiment of this invention as a plastic blow container for medicinal fluids, backpressure is applied during natural dripping and a very efficient natural dripping mode can be obtained. Medicinal fluid accumulating capability is large and dripping proceeds without forming dead space.

INDUSTRIAL APPLICABILITY

In the above manner, this invention is applicable for use as an internally filled container for medicinal fluids such as sugar solutions, electrolytic solutions, blood sugar amplifiers, osmotic diuretics, amino acid solutions, fat emulsion preparations, high calorie solutions, enteral nutrients, high protein nutrients, elemental nutrients and liquid foods.

We claim:

1. A plastic container for medicinal fluids, comprising:

a flat shaped body portion having a cross-sectional shape such that a longer width-wise dimension thereof is more than 2.0 times a shorter width-wise dimension thereof, and having first faces parallel to a longitudinal axis and second faces parallel to a transverse axis which is perpendicular to the longitudinal axis wherein said larger width-wise dimension and shorter width wise dimension terminate at a point of intersection where said first and second faces meet;

a suspension portion formed at an upper end of said flat shaped body portion with a tapered shape extending upwardly; and said flat shaped body portion having a convex, wedge shaped upper tapered end and a convex wedge, shaped lower tapered funnel end wherein a center portion of said flat shaped body portion has an opening formed therein, the funnel end being defined by first end portions connected to said first parallel faces of said flat shaped body portion on sides along a shorter width-wise axis that converge toward the opening and second end portions connected to said second parallel faces of said flat shaped body portion on sides along a longer width-wise axis that converge toward the opening.

2. The plastic blow container for medicinal fluids according to claim 1, wherein said wedge shape forms an angle $\alpha$ of less than 60 degrees and said tapered funnel shape forms an angle $\beta$ of less than 130 degrees.

* * * * *

UNITED STATES PATENT AND TRADEMARK OFFICE
CERTIFICATE OF CORRECTION

PATENT NO. : 5,632,738
DATED : May 27, 1997
INVENTOR(S) : Takehiko SUMI, et al.

It is certified that error appears in the above-indentified patent and that said Letters Patent is hereby corrected as shown below:

On the title page, Item [63], the Related U.S. Application Data should read:

--Continuation of Ser. No. 39,335, filed as PCT/JP91/01209, Sep. 12, 1991 published as WO 93/04657, Mar. 18, 1993 abandoned.--

Signed and Sealed this

Sixteenth Day of September, 1997

Attest:

BRUCE LEHMAN

*Attesting Officer*

*Commissioner of Patents and Trademarks*